Figure 1:
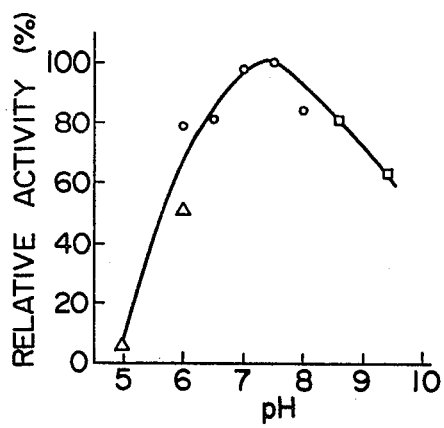

United States Patent

Kubo et al.

[11] 4,438,201
[45] Mar. 20, 1984

[54] AMIDOHYDROLASE HAVING ABILITY TO DEPANTOTHENYLATE AN ANTIBIOTIC

[75] Inventors: Katsuro Kubo, Fijisawa; Yasuo Fukagawa, Kamakura; Tomoyuki Ishikura, Chigasaki, all of Japan

[73] Assignee: Sanraku-Ocean Co., Ltd., Tokyo, Japan

[21] Appl. No.: 394,169

[22] Filed: Jul. 1, 1982

[30] Foreign Application Priority Data

Jul. 1, 1981 [JP] Japan ............................... 56-101161

[51] Int. Cl.³ ...................... C12N 9/80; C12P 17/18; C12R 1/465
[52] U.S. Cl. .................................. 435/228; 435/119; 435/886
[58] Field of Search ...................... 435/228, 119, 121

[56] References Cited

U.S. PATENT DOCUMENTS 4,282,322 8/1981 Kahan et al. ........................ 435/228

*Primary Examiner*—Lionel M. Shapiro
*Attorney, Agent, or Firm*—Wenderoth, Lind & Ponack

[57] ABSTRACT

A novel enzyme, amidohydrolase, having the ability to depantothenylate antibiotic OA-6129A represented by the following formula

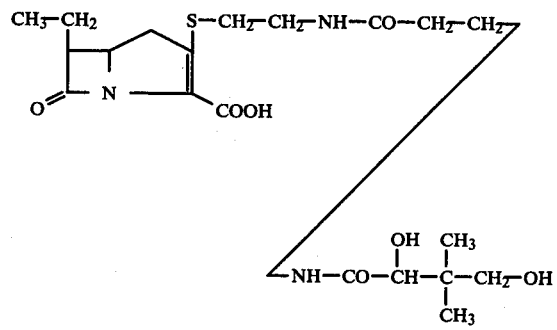

but no substantial ability to deacetylate antibiotic PS-5 represented by the following formula

4 Claims, 4 Drawing Figures

△ ACETATE BUFFER
○ PIPES BUFFER
□ VERONAL BUFFER

△ ACETATE BUFFER
○ PIPES BUFFER
□ VERONAL BUFFER

AMIDOHYDROLASE HAVING ABILITY TO DEPANTOTHENYLATE AN ANTIBIOTIC

This invention relates to a novel enzyme, and more specifically, to amidohydrolase having the ability to depantothenylate antibiotic OA-6129A of the following formula

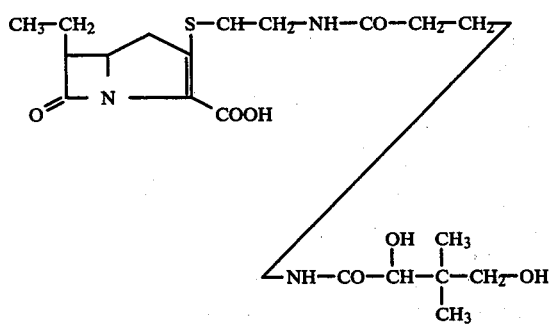

but no substantial ability to deacetylate antibiotic PS-5 of the following formula

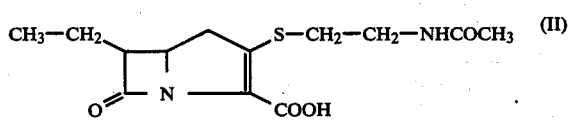

The present inventors previously found that *Streptomyces fulvoviridis* A933 (FERM BP-10) produced antibiotic PS-5 of formula (II) [Journal of Fermentation Technology, Vol. 57 (1979), pages 265-272] and Streptomyces sp. OA-6129 (FERM BP-11) produced antibiotic OA-6129A of formula (I) (see Japanese Patent Application No. 135829/1980).

In order to study the mechanisms of biosynthesis of antibiotics PS-5 and OA-6129A, the present inventors examined the biochemical differences of the two Streptomyces strains, and found that these strains specifically differ in the productivity of a certain enzyme. This enzyme has now turned out to be the aforesaid novel amidohydrolase.

The amidohydrolase provided by this invention is multifunctional and has the following characteristics.

(1) The amidohydrolase of the invention has the ability to cleave the pantotheinyl group represented by the following formula

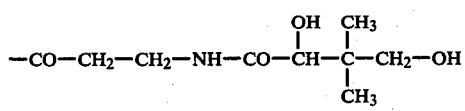

from the C-3 pantotheinyl side-chain of antibiotic OA-6129A of formula (I), but no substantial ability to cleave the acetyl group from the C-3 acetylaminoethylthio side-chain of antibiotic PS-5 of formula (II). Thus, the amidohydrolase of the invention is characterized by substrate specificity to the pantotheinyl group.

(2) The amidohydrolase of the invention generally has the properties of L-amino acid acylase. More particularly, it is N-acyl-2-amino acid amidohydrolase which removes the N-acyl group from N-acyl-L-amino acids such as N-chloroacetyl-L-phenylalanine, but not from N-acyl-D-amino acids.

(3) The amidohydrolase of the invention, as is known in the case of penicillin acylase, may have an activity of transferring the acyl group from acyl-coenzyme A (CoA) to certain substrates having a free amino group and/or an activity of exchanging the acyl group of an acyl-donor with the amide-forming acyl group of an acceptor. For example, it catalyzes the exchange of the C-3 pantotheinyl group of antibiotic OA-6129A of formula (I) with the acyl group of acetyl-CoA, propionyl-CoA, butyryl-CoA or glutaryl-CoA; and/or the transfer of the acyl group from acetyl-CoA, propionyl-CoA, butyryl-CoA or glutaryl-CoA in the amino group of 6-aminopenicillanic acid (6-APA) or NS-5.

The amidohydrolase of the invention can usually be produced by cultivating a carbapenem-producing strain of the genus Streptomyces in a nutrient medium, and recovering aminohydrolase having the above-described properties by a method known per se.

The carbapenem-producing strains of the genus Streptomyces which can be used in the production of the amidohydrolase include microorganisms capable of producing antibiotics having a carbapenem skeleton of the following formula

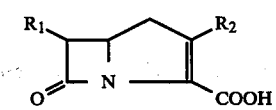

for example thienamycin [R$_1$=CH$_3$CH(OH)— and R$_2$=—SCH$_2$CH$_2$NH$_2$; J. Antibiotics, 32, 1-12 (1979)], N-acetylthienamycin [R$_1$=CH$_3$CH(OH)— and R$_2$=SCH$_2$CH$_2$NHCOCH$_3$; Japanese Laid-Open Patent Publication No. 65294/1977], N-acetyldehyrothienamycin [R$_1$=CH$_3$CH(OH)— and R$_2$=—SCH=CHNH-COCH$_3$; Japanese Laid-Open Patent Publication No. 130494/1978], epithienamycins A and C [R$_1$=CH$_3$CH(OH)— and R$_2$=—SCH$_2$CH$_2$NH-COCH$_3$] and B and D [R$_1$=CH$_3$CH(OH)— and R$_2$=—SCH=CHNHCOCH$_3$][Japanese Laid-Open Patent Publications Nos. 65293/1977 and 131596/1977], MM 17880 [R$_1$=CH$_3$CH(OSO$_3$H)— and R$_2$=—SCH$_2$CH$_2$NHCOCH$_3$; J. Antibiotics, 32, 295-304 (1979)], MM 13902 [R$_1$=CH$_3$CH(OSO$_3$H)— and R$_2$=—SCH=CHNHCOCH$_3$; J. Antibiotics, 32, 295-304 (1979)], MM 4550 [R$_1$=CH$_3$CH(OSO$_3$H)— and R$_2$=

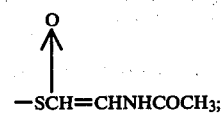

J. Antibiotics, 32, 295-304 (1979)], antibiotic PS-5 [R$_1$=CH$_3$CH$_2$— and R$_2$=—SCH$_2$CH$_2$NHCOCH$_3$; J. Antibiotics, 33, 796-803 (1980)], antibiotic PS-6 [R$_1$=(CH$_3$)$_2$CH— and R$_2$=—SCH$_2$CH$_2$NHCOCH$_3$; J. Antibiotics, 33, 1128-1137 (1980)], antibiotic PS-7 [R$_1$=CH$_3$CH$_2$— and R$_2$=—SCH=CHNHCOCH$_3$; J. Antibiotics, 33, 1128-1137 (1980)], antibiotic PS-8 [R$_1$=(CH$_3$)$_2$CH— and R$_2$=—SCH=CHNHCOCH$_3$; Japanese Laid-Open Patent Publication No. 25183/1981], carpetimycin A [R$_1$=(CH$_3$)$_2$(OH)C— and R$_2$=

J. Antibiotics, 33, 1388–1389 (1980)], C-19393 S₂
[R₁=(CH₃)₂C(OSO₃H)— R₂=

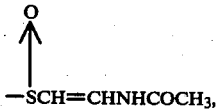

J. Antibiotics, 33, 1425–1430 (1980)], PA-31088-IV
[R₁=HOCH₂C(CH₃)= and R₂=

Japanese Laid-Open Patent Publication No. 136282/1980].

Specific examples of these strains include the following:

*Streptomyces fulvoviridis* (ATCC 15863 and 21954 and FERM P-3935–3937),
*Streptomyces cattleya* (NRRL 8057),
*Streptomyces flavogriseus* (NRRL 8139 and 8140),
*Streptomyces olivaceus* (ATCC 21379–21382, 31126 and 31365, and NCIB 8238 and 8509),
*Streptomyces gedanensis* (ATCC 4880),
*Streptomyces argenteolus* (ATCC 11009),
*Streptomyces flavovirens* (ATCC 3320),
*Streptomyces flavus* (ATCC 3369),
*Streptomyces siovaensis* (ATCC 13989),
*Streptomyces cremeus* subsp. *auratilis* (ATCC 31358),
*Streptomyces fulvoviridis* A933 (FERM BP-10),
Streptomyces sp. KC-6643 (FERM P-4467),
*Streptomyces griseus* subsp. *cryophilus* (IFO 13886), and
*Streptomyces tokunonensis* (FERM P-4843).

Of these microorganisms, *Streptomyces fulvoviridis*, *Streptomyces cattleya*, *Streptomyces cremeus* subsp. *auratilis*, and *Streptomyces argenteolus* are preferred, and *Streptomyces fulvoviridis* A933 is especially preferred.

The microbiological properties of *Streptomyces fulvoviridis* A933 are as follows:

(1) Morphology

Under a microscope, straight to flexuous aerial mycelia without verticillate branches are seen to grow from well-branched substrate mycelia. The mature spore chain consists of 10 to 50 elliptical to cylindrical spores, and no sporangium is noted. The spores are about (0.8~1.0)×(0.7~2.5) microns in size and have smooth surfaces. No flagellated spore is observed.

(2) Growth in various culture media

Cultivation is carried out at 28° to 30° C. unless specifically indicated otherwise. The colors are described mainly in accordance with the method described by H. D. Tresner and E. J. Backus (Journal of Applied Microbiology, Vol. 11, No. 4, pages 335 to 338 (1963)), and the symbols shown in the parentheses [ ] (CHM code) refer to those given in Color Harmony Manual of Container Corporation of America.

(1) Sucrose-nitrate agar

Light brownish gray [3fe] to brownish gray [5ih] aerial mycelia occur on a moderate growth tinted with yellowish gray [2dc] to gray [2fe]. No soluble pigment is observed.

(2) Glucose-asparagine agar

Light brownish gray [3fe] to dark gray [3ih] aerial mycelia occur on a good growth tinted with light yellow [1½fb–2fb]. No soluble pigment is observed.

(3) Glycerol-asparagineagar (ISP medium-5)

Light gray [d] to light grayish red brown [5fe] aerial mycelia occur on a good growth tinted with grayish yellow [3ec] and partly with light brownish gray [3fe]. No soluble pigment is observed.

(4) Starch-inorganic salt agar (ISP medium-4)

Dark gray [3ih] aerial mycelia occur on a good growth tinted with pale yellow [2db] to pale yellowish green [241/2dc]. No soluble pigment is observed.

(5) Tyrosine-agar medium (ISP medium-7)

Slightly greenish light gray [d] aerial mycelia occur on a good growth tinted early with light yellow [2fb] and later with light olive brown [2ge]. The medium is colored brown very slightly.

(6) Nutrient agar

Light gray [d] aerial mycelia occur on a moderate growth tinted with light brownish gray [3fe]. No soluble pigment is observed.

(7) Yeast extract-malt extract agar

Light brownish gray [2fe] to brownish gray [5ih] aerial mycelia occur on a good growth tinted with white [b]. No soluble pigment is observed.

(8) Oatmeal agar (ISP medium-3)

Light brownish gray [3fe] to dark gray [3ih] aerial mycelia occur on a good growth tinted with dark gray [3ih]. No soluble pigment is observed.

(9) Calcium malate agar

Light grayish brown [3fe] aerial mycelia occur on a moderate growth tinted with light olive brown [2ge]. No soluble pigment is observed.

(10) Peptone-yeast extract-iron agar (ISP medium-6)

Pale white [w] to light gray [d] aerial mycelia occur on a good growth tinted with pale yellow [2db].

(3) Physiological properties (1) Growth temperature range

Experiments were conducted on yeast extract-malt extract agar (ISP medium-2) at a temperature of 10°, 20°, 25°, 30°, 34°, 37°, 40°, 45°, and 50° C. The strain scarcely grew at 37° C., and did not grow above 40° C. at all. At the other temperatures, its growth was observed. The optimum growth temperature seems to be in the range of 20° to 30° C.

(2) Liquefaction of gelatin: positive (3) Hydrolysis of starch: positive (4) Coagulation and peptonization of skimmed milk: Peptonized without coagulation.

(5) Reduction of nitrate: positive (6) Formation of a melanoid pigment

No melanoid pigment is formed in a peptone-yeast extract-iron agar medium (ISP medium-6) and a tyrosine agar medium. In trypton-yeast extract broth, a very slightly brown color is formed.

(4) Utilization of various carbon sources (in Pridham Gottlieb agar)

(1) L-Arabinose: +
(2) D-Xylose: +

(3) D-Glucose: +
(4) D-Fructose: +
(5) Sucrose: ±
(6) Inositol: ±
(7) L-Rhamnose: +
(8) Raffinose: −
(9) D-Mannitol: +
+: utilized; −: not utilized Streptomyces fulvoviridis A933 having the above-described microbiological properties was deposited on June 20, 1981 in accordance with the Budapest Treaty with the accession number of No. 10 (FERM BP-10) at Fermentation Research Institute, Agency of Industrial Science and Technology, Japan.

Nutrient sources usually employed for the cultivation of actinomycetes can be used for cultivation of the aforesaid carbapenem-producing microorganisms of the genus Streptomyces. They include carbon sources, for example carbohydrates such as glucose, glycerol, maltose, sucrose, molasses, dextrin and starch and oils and fats such as soybean oil, peanut oil and lard; nitrogen sources such as peptone, meat extract, soybean meal, cottonseed meal, dried yeast, corn steep liquor, yeast extract, skimmed milk, casein, sodium nitrate, ammonium nitrate and ammonium sulfate; and inorganic salts such as dipotassium phosphate, sodium chloride, calcium carbonate and magnesium sulfate. As required, traces of metals such as cobalt and manganese can be added. Any other nutrient sources can be used as far as the production of the amidohydrolase of the invention by Streptomyces is supported. In order to control foaming during sterilization and cultivation, antifoamers such as silicones and vegetable oils may be added.

The mixing ratio of the aforesaid nutrient sources is not critically restricted, and can be varied over a wide range. The optimum compositions and mixing ratios of nutrient sources for a particular microorganism can be easily determined by anyone skilled in the art through small-scale experiments.

The nutrient medium may be sterilized prior to cultivation. Advantageously, the pH of the culture medium is adjusted to a range of 4 to 9, preferably a range of 6 to 8, before or after sterilization.

Cultivation of the above-described microorganisms in such nutrient media can be carried out by methods usually employed for the production of antibiotics by actinomycetes. Usually, the cultivation is suitably carried out under aerobic conditions, for example, with stirring and/or forced aeration. Although the method of cultivation may be stationary, shaken, or submerged with aeration and agitation, the submerged cultivation is advantageous.

The cultivation temperature may vary depending upon the producing strain. Generally, the suitable temperature is 20° to 40° C., preferably 25° to 35° C.

For better cultivation, the pH of the culture broth may be adjusted to 4 to 9, especially 6 to 8, during cultivation as necessary.

In the case of large-scale fermentation intended for mass production, it is more advantageous to perform seed cultivation before the main cultivation in a production medium under submerged conditions.

The cultivation time varies depending upon the composition of the medium, the cultivation temperature, the producing strain, etc. Usually, it is in the range of 30 to 90 hours.

Anyone skilled in the art can easily determine the optimum cultivation conditions for a particular producing strain through simple experiments.

Extraction and purification of the enzyme of the invention can be carried out by commonly used methods. For example, the microbial cells are separated from the culture broth by a suitable method such as refrigerated centrifugation. The separated cells are then broken by physical grinding with sand or glass powder, treatment with a lytic enzyme such as lysozyme, sonication, osmotic shock, or the like. Or the cells are shaken or allowed to stand in the presence of toluene or a surface active agent such as sodium cholate or Triton X-100 so that the enzyme of the invention is released from the cells. The crude enzyme solution is separated from the debris by a suitable method such as filtration or centrifugation, or directly obtained by extracting the cells with an appropriate buffer or organic solvent. The crude enzyme solution may be converted to a powder by a usual method such as lyophilization, alcohol precipitation, acetone precipitation, or the like.

A purified enzyme preparation may be obtained from the crude enzyme solution or powder by a suitable combination of gel filtration on Sephadex ® or Biogel ®, column chromatography using an ion exchanger, gel electrophoresis using polyacrylamide gel, column chromatography on hydroxyapatite, sucrose density gradient centrifugation, affinity chromatography, ultrafiltration, etc.

The autolysate of the culture broth may similarly be treated to give preparations of the enzyme of this invention.

The following examples illustrate the present invention in detail.

EXAMPLE 1

Glycerol (36 g), 13.5 g of Essan-Miit ® (soybean meal; a product of Ajinomoto Co., Ltd.), 4.5 g of fish meal, 0.9 g of $K_2HPO_4$, 0.9 g of $MgSO_4.7H_2O$, and 1.35 g of $CaCO_3$ were dissolved in 450 ml of tap water and adjusted to pH 7.2. Fifteen milliliter portions of the suspension were put in 250 ml Erlenmeyer flasks, and autoclaved at 120° C. for 15 minutes. After cooling, Streptomyces fulvoviridis A933 (FERM BP-10) was inoculated in the flasks and cultivated at 28° C. for 68 hours with shaking. The culture broth was centrifuged and the cells were washed twice with 0.01 M potassium phosphate buffer, pH 7.1, and then suspended in 100 ml of the same buffer. The suspension was subjected to ultrasonication treatment (20 KHz, 60 W) for 5 minutes and centrifuged to give 80 ml of a crude homogenate. Powder of solid ammonium sulfate was added to the homogenate under stirring at 4° C. to reach 60% saturation. Following refrigerated centrifugation, the precipitate was dissolved in a small amount of 0.01 M potassium phosphate buffer, pH 7.1, dialyzed against the same buffer, and then adsorbed onto a column (2×40 cm) of a DEAE-Sephacel ® (a product of Pharmacia Fine Chemicals AB). The column was washed with the same buffer, and eluted with a linear concentration gradient of NaCl from 0.1 M to 0.4 M in the same buffer. The active fractions (200 ml in total) were concentrated with Collodion Bag 25 ® (a product of Sartorius GmbH), dialyzed against 0.01 M potassium phosphate buffer, pH 7.1, and adsorbed onto a column (1.5×15 cm) of DEAE-Sephadex ® (a product of Pharmacia Fine Chemicals AB) which had been equilibrated with the same buffer. The column was washed with the same buffer and eluted with the same buffer containing 0.25 M NaCl to give 65 ml of active fractions. The active solution was concentrated with Collodion Bag 25, dialyzed against 0.01 M potassium phosphate buffer, and subjected to preparative isoelectric focusing using polyacrylamide gel and Ampholine ® (pH 4–6) (a product of LKB-Producter AB). Active fractions were combined, and subjected to gel filtration on a column (1.9×60 cm) of Sephadex G-150 (a product of Pharmacia Fine Chemicals AB) which had been equilibrated with 0.01 M potassium phosphate buffer, pH 7.1. After concentration with Collodion Bag 25, the enzyme solution was again purified by gel filtration on a column (1.9×60 cm) of Sephadex G-150. Fifteen ml of the active fractions were concentrated with Collodion Bag 25 to give 1.5 ml (270 µg protein in total) of a standard preparation of the enzyme of this invention.

The enzyme preparation was analyzed by disc gel electrophoresis at a pH of 8.3, followed by staining with Coomassie Brilliant Blue R. The relative mobility ($Rm_{BPB}$) of the enzyme against bromophenol blue (indicator) was 0.52. In addition to this major band, one minor band was observed at $R_{mBPB}$ 0.33. Based on this result, the purity of the enzyme preparation was determined to be more than 95%.

The enzymological properties of the enzyme preparation are as follows:

(1) Activities (a) It has the ability to depantothenylate a compound of the following formula (III).

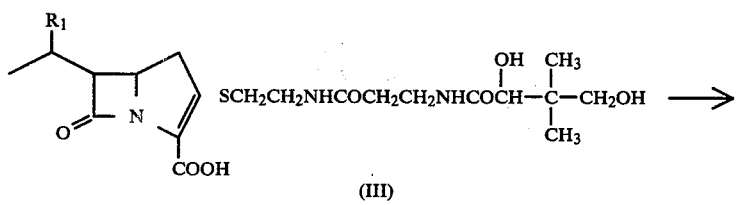

(III)

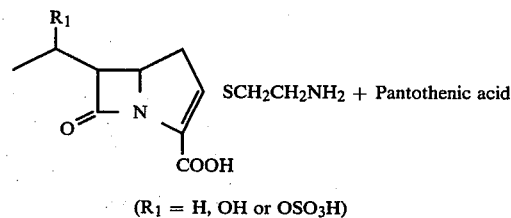

($R_1$ = H, OH or $OSO_3H$)

Details of this reaction are shown in Experiment A given hereinbelow.

(b) It has the ability to deacylate N-acyl-L-amino acid.

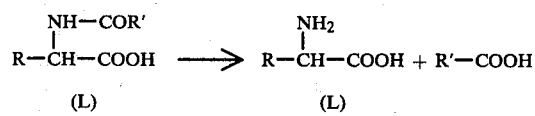

(R = an organic group; R'CO = acyl)

It does not substantially act on N-acyl-D-amino acids.

(c) It has the ability to transfer the acyl group to the amino group of the C-3 side chain of the OA-6129 group of carbapenems and 6-aminopenicillanic acid (Reactions 1 and 3) and to exchange the acyl group of acyl-CoA with the pantotheinyl group of the C-3 pantetheinyl side chain of the OA-6129 group of carbapenems (Reaction 2).

Reaction 1

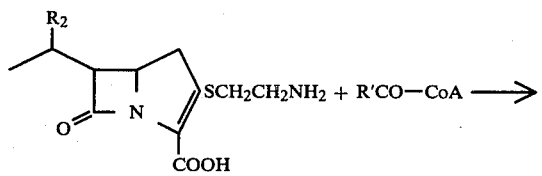

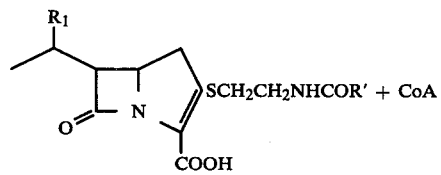

(R'CO = acyl; $R_2$ = H, OH or $OSO_3H$)

Reaction 2

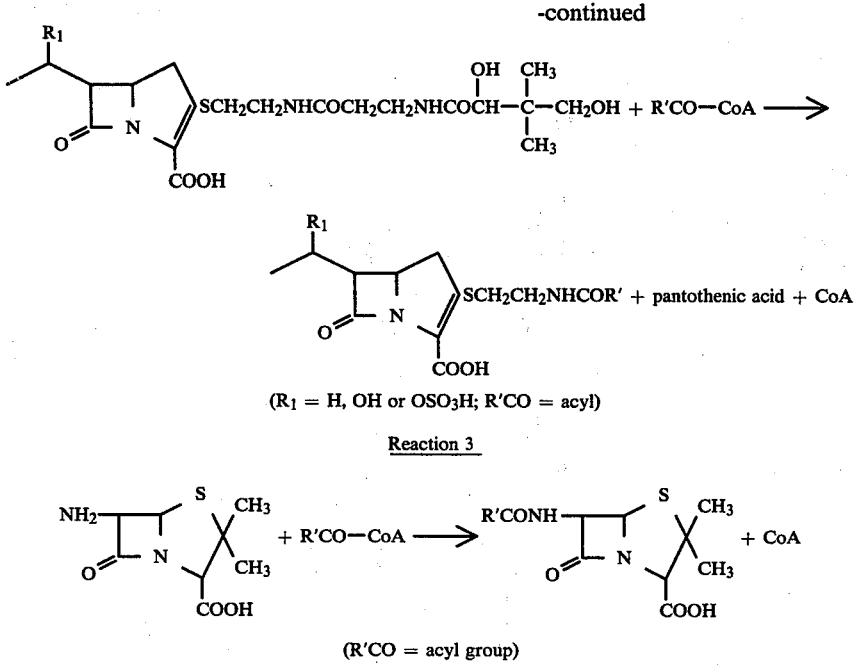

(R₁ = H, OH or OSO₃H; R'CO = acyl)

Reaction 3

(R'CO = acyl group)

Details of these reactions are shown in Experiments B and C given hereinbelow.

(2) Substrate specificity

Table 1 shows the substrate specificity of the enzyme of this invention for N-acyl-amino acids. The relative activity in Table 1 refers to N-chloroacetyl-L-phenylalanine as 100.

TABLE 1

| N—Acyl-amino acid | Relative activity |
|---|---|
| N—Formyl-L-methionine | 112.7 |
| N—Formyl-L-leucine | 16.4 |
| N—Acetyl-glycine | 23.9 |
| N—Acetyl-L-alanine | 163.8 |
| N—Acetyl-D-alanine | 0 |
| N—Acetyl-L-valine | 32.4 |
| N—Acetyl-D-valine | 0 |
| N—Acetyl-L-methionine | 262.1 |
| N—Acetyl-D-methionine | 0 |
| N—Acetyl-L-leucine | 92.8 |
| N—Acetyl-D-leucine | 0 |
| N—Acetyl-L-phenylalanine | 15.3 |
| N—Acetyl-D-phenylalanine | 0 |
| N—Acetyl-L-glutamic acid | 2.7 |
| N—α-Acetyl-L-lysine | 39.8 |
| N—Chloroacetyl-L-valine | 351.1 |
| N—Chloroacetyl-L-leucine | 348.5 |
| N—Chloroacetyl-L-phenylalanine | 100 |

(3) Optimum reaction pH and pH stability.

The optimum pH is determined by measuring the relative deacylation activities with N-chloroacetyl-L-phenylalanine under standard assay conditions described in section (4) below except that the following buffers were used at the indicated pH values.

Acetate buffer (pH 5–6)
PIPES buffer (pH 6–8)
Veronal buffer (pH 8–9.5)

The results are summarized in FIG. 1, indicating that the optimum pH is 7 to 7.5.

Figure 2:
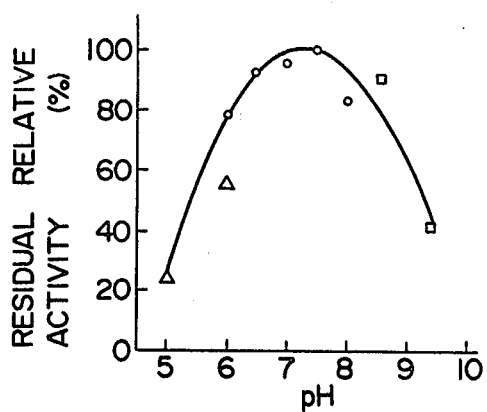

The pH stability of the enzyme is examined as follows: After the enzyme is left to stand at 6° C. for 15 hours at the indicated pH values, the remaining enzyme activity is measured under the standard assay conditions. The results are shown in FIG. 2. It is clear from FIG. 2 that the enzyme is stable at a pH in the range of 6 to 8.

(4) Measurement of enzyme activity

Ten microliters of 0.2 M piperazine-N,N'-bis(2-ethanesulfonic acid) [=PIPES] buffer, pH 7.3, and 10 μl of 100 mM N-chloroacetyl-L-phenylalanine (adjusted to pH 6-7 with NaOH) are dissolved in 20 μl of water. After 10 μl of an enzyme solution (30–50 μg/ml) is added, the mixture is incubated at 37° C. for 15 minutes. Then, 50 μl of 50% acetic acid is added to stop the enzymatic reaction. The amount of L-phenylalanine produced from the substrate in the reaction solution is determined by the Yemm-Cocking ninhydrin colorimetric method (E. W. Yemm & E. C. Cocking: Analyst, Vol. 80, page 209, 1955) or with an amino acid automatic analyzer (Model 835-50, Hitachi Limited).

The specific activity of the standard enzyme preparation described above was found to be 11.9 μmoles/min./mg enzyme protein with N-chloroacetyl-L-phenylalanine. The concentration of protein is determined by the UV method of Whitaker and Granum (J. R. Whitaker & P. E. Granum: Anal. Biochem., Vol. 109, page 156, 1980).

(5) Optimum reaction temperature

Figure 3:
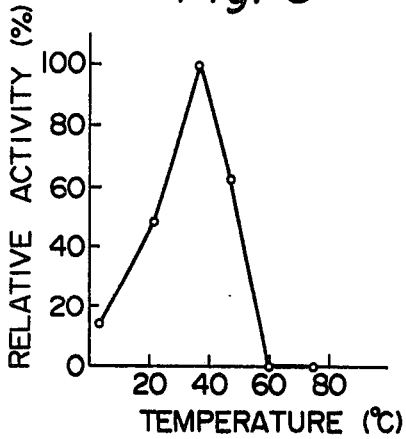

The enzyme activity of the standard preparation is measured at the indicated temperatures under the standard assay conditions shown in (4) above. The relative activity is plotted against the reaction temperature (in FIG. 3), showing that the optimum reaction temperature is 25° to 45° C.

(6) Inactivation conditions

As shown in FIG. 2, when incubated at 6° C. for 15 hours, the enzyme is inactivated by 75% and 60% at a pH of 5 and 9.5, respectively. The thermal inactivation of the enzyme of the invention is examined by incubating the enzyme solution at various temperatures for 15 hours in PIPES buffer, pH 7.3, followed by measuring the residual relative activity (%).

Figure 4:
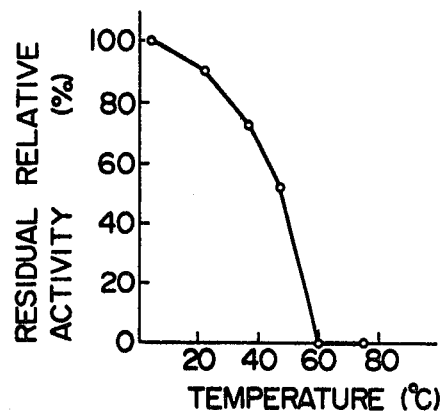

The results are shown in FIG. 4. It is apparent from FIG. 4 that the present enzyme is inactivated to an extent of 50% at 50° C., and is completely inactivated at 60° C.

(7) Inhibitors, activators, and stabilizers

Table 2 shows the effects on the present enzyme of various metal ions, chelating agents, —SH inhibitors, etc. measured at indicated final concentrations.

The relative activity in Table 2 refers to the activity of the enzyme in the absence of such chemical as 100.

Many known acylases (N-acylamino acid amidohydrolases) are activated or stabilized by the addition of $Co^{++}$ (in a concentration range of 0.5 to 10 mM), whereas the enzyme of this invention is inhibited by it.

TABLE 2

| Additive | Concentration | Relative activity |
|---|---|---|
| $HgCl_2$ | 1 mM | 0 |
| $HgCl_2$ | 0.1 mM | 6.4 |
| $HgCl_2$ | 0.01 mM | 84.5 |
| $CuCl_2$ | 1 mM | 0 |
| $CuCl_2$ | 0.1 mM | 87.5 |
| $ZnCl_2$ | 1 mM | 7.7 |
| $CdCl_2$ | " | 10.2 |
| $FeSO_4$ | " | 53.2 |
| $PbCl_2$ | " | 58.8 |
| $SnCl_2$ | " | 64.4 |
| $MnCl_2$ | " | 74.3 |
| $NiSO_4$ | " | 79.4 |
| $MgCl_2$ | " | 93.6 |
| $CoCl_2$ | 0.2 mM | 92.3 |
| $CoCl_2$ | 1 mM | 82.4 |
| $CoCl_2$ | 2 mM | 3.8 |
| $CoCl_2$ | 4 mM | 0 |
| EDTA* | 1 mM | 95.8 |
| o-PT** | " | 56.4 |
| p-CMB*** | " | 0 |

(note)
*EDTA: ethylenediaminetetracetic acid
**o-PT: o-phenanthroline
***p-CMB: p-chloromercuribenzoic acid (8) Molecular weight The enzyme of this invention has a molecular weight of about 100,000 on gel filtration using Sephadex G-150.

(9) Isoelectric point

The enzyme of this invention has an isoelectric point (pI) of 5.1, when measured by isoelectric focusing using polyacrylamide gel and Ampholine ® (pH 3–10).

(10) Disc gel electrophoresis

The enzyme of this invention has a relative mobility ($R_{mBPB}$) of 0.52 as determined by disc gel electrophoresis using bromophenol blue as indicator.

EXPERIMENT A

A mixture (50 μl) consisting of 10 μl of 0.2 M potassium phosphate buffer, pH 7.4, 20 μl of an antibiotic PS-5 solution (500 μg/ml) or an antibiotic OA-6129A solution (500 μg/ml), 10 μl of the enzyme solution obtained in Example 1, and 10 μl of water was incubated at 37° C. for 3 hours.

As a control, the mixture minus the enzyme solution was allowed to react under the same conditions.

3 μl of each of the resulting reaction solutions was spotted on Watmann No. 1 filter paper, and subjected to electrophoresis for 50 minutes at 1500 V/30 cm with Veronal buffer, pH 8.6. After electrophoresis, the products were bioautographed with Comamonas terrigena B-996 as assay organism. It was found that the PS-5 reaction solutions, irrespective of the presence and absence of the enzyme, gave only one antimicrobial spot at 6.5 cm from the origin towards the anode which was identified with PS-5. This finding means that the present enzyme did not attack antibiotic PS-5 at all.

The OA-6129A reaction mixture containing no enzyme produced an antibacterial spot at 4.4 cm towards the anode which corresponded with OA-6129A, whereas the mixture containing the enzyme yielded a halo at 1 cm to the cathode. By direct comparison, the latter halo was identified with N-deacylated antibiotic PS-5 (to be referred to as antibiotic NS-5).

When the latter OA-6129A reaction solution was bio-assayed by pantothenate-requiring Saccharomyces carlsbergensis (ATCC 9080) as assay organism, the concentration of pantothenate was found to be 8 μg/ml.

The above-described results demonstrate that the present enzyme removes the pantotheinyl group from antibiotic OA-6129A to give antibiotic NS-5 and pantothenate.

EXPERIMENT B

A mixture consisting of 10 μl of 0.2 M potassium phosphate buffer, pH 7.4, 10 μl of a solution of antibiotic OA-6129A (500 μg/ml), 10 μl of acyl-CoA (5 μmoles/ml), 10 μl of the enzyme preparation from Example 1 and 10 μl of water was allowed to react at 37° C. for 3 hours. The product was assayed by high voltage paper electrophoresis (HVPE) in the same way as in Experiment A.

As controls, the same mixture minus acyl-CoA and the same mixture minus the enzyme solution were incubated under the same conditions as mentioned above.

Acetyl-CoA, n-propionyl-CoA, n-butyryl-CoA and glutaryl-CoA were used as acyl-CoA.

The absence of the enzyme resulted in detection of the substrate (antibiotic OA-6129A) at 4.5 cm to the anode. The reaction mixture containing the enzyme but no acyl-CoA yielded only one spot at 1 cm to the cathode (antibiotic NS-5), as is explained in Experiment A. When acyl-CoA and the enzyme were present in the reaction mixtures, two antibacterial spots were detected which corresponded with antibiotic NS-5 and N-acyl antibiotic NS-5 respectively. More particularly, a new antibacterial spot was observed at 6.5 cm to the anode (the same position as PS-5), when acetyl-CoA, n-propionyl-CoA or n-butyryl-CoA was added. Glutaryl-CoA produced a growth inhibition zone at 11.2 cm to the anode.

These results demonstrate that in the presence of acyl-CoA, the present enzyme catalyzes the exchange of the pantotheinyl group of antibiotic OA-6129A with the acyl group of acyl-CoA.

EXPERIMENT C 0.2 M Potassium phosphate buffer, pH 7.4 (10 μl), 10 μl of 6-aminopenicillanic acid (6-APA) (500 μg/ml), 20 μl of acyl-CoA (5 μmoles/ml) and 10 μl of the enzyme preparation from Example 1 were mixed and incubated at 37° C. for 3 hours. The products were analyzed by HVPE in the same way as in Example 2, employing acetic acid buffer, pH 4.5 Acetyl-CoA and glutaryl-CoA were used as acyl-CoA.

The controls were the same reaction mixtures minus enzyme solution and acyl-CoA respectively.

With the two control reaction mixtures, an antibacterial spot was observed only at 0.7 cm to the anode which was ascribed to 6-APA. When acetyl-CoA was added, two antibacterial spots were observed at 0.7 cm and 5.3 cm to the anode. Glutaryl-CoA yielded halos at 0.7 cm and 6.2 cm to the anode.

The foregoing results show that 6-APA was converted to the corresponding acyl-6-APA by the action of the present enzyme and acyl-CoA.

EXAMPLE 2

Glucose (2.5 g), 1 g of corn steep liquor, 0.5 g of Pharmamedia ® (a product of Traders Oil Mill Company), 0.5 g of yeast extract and 0.3 g of $CaCO_3$ were dissolved in 100 ml of tap water, and the pH of the suspension was adjusted to 7.0. Then, 50 ml portions of the suspension were distributed in 250 ml Erlenmeyer flasks, and sterilized at 120° C. for 15 minutes. After cooling *Streptomyces cattleya* (NRRL 8057) was inoculated, and the flasks were cultivated at 28° C. for 90 hours with shaking.

Mycelia were collected by centrifugation and treated by the same procedure as in Example 1 to give 20 ml of a cell-free homogenate. With this fresh homogenate, the enzymological properties of *Streptomyces cattleya* acylase were examined.

A mixture containing 10 μl of 0.2 M potassium phosphate buffer, pH 7.4, 10 μl of an antibiotic PS-5 solution (500 μg/ml) or an antibiotic OA-6129A solution (500 μg/ml), 10 μl of acyl-CoA (5 μmoles/ml) and 20 μl of the cell-free homogenate was incubated at 37° C. for 4 hours. The product was analysed by HVPE in the same manner as in Experiment A.

The control reaction mixtures contained either no cell-free homogenate or no acyl-CoA. Acetyl-CoA and n-propionyl-CoA were used as acyl-CoA.

When antibiotic PS-5 was used as substrate, only the antibacterial spot of the substrate (antibiotic PS-5) was observed at 6.8 cm to the anode, indicating that antibiotic PS-5 was not susceptible to the cell-free homogenate of *Streptomyces cattleya*, irrespective of the presence of acyl-CoA. *Streptomyces cattleya* could catalyze not only the deacetylation of antibiotic PS-5, but also the acyl transfer or exchange from acyl-CoA.

When antibiotic OA-6129A was used as substrate, on the other hand, a single antibacterial spot was observed at 4.5 cm to the anode corresponding with antibiotic OA-6129A in the absence of the cell-free homogenate extract. Deletion of acyl-CoA from the reaction mixture led to the production of NS-5 at 1.1 cm to the cathode, whereas the presence of acetyl-CoA caused antibiotic OA-6129A to transform to PS-5.

The above-mentioned findings demonstrate that the cell-free homogenate of *Streptomyces cattleya* catalyzes the depantothenylation of antibiotic OA-6129A to produce antibiotic NS-5; and the acyl exchange of OA-6129A with acyl-CoA via antibiotic NS-5.

EXAMPLE 3

Soluble starch (5.2 g), 1.2 g of Essan-Miit, 0.16 g of NaCl, 0.08 g of $K_2HPO_4$ and 0.04 g of $MgSO_4.7H_2O$ were dissolved in 80 ml of tap water and 40 ml portions of the suspension were filled in two 250 ml Erlenmeyer flasks. After autoclaving at 120° C. for 15 minutes, *Streptomyces cremeus* subsp. *auratilis* was inoculated, and cultivated at 28° C. for 68 hours. Using the same procedure as in Example 1, 20 ml of the cell-free homogenate was obtained. For confirmation of the enzyme activity, the following reactions were studied.

A mixture (50 μl) consisting of 10 μl of 0.2 M potassium phosphate buffer, pH 7.4, 10 μl of an antibiotic PS-5 solution (500 μg/ml) or an antibiotic OA-6129A solution (500 μg/ml), 20 μl of the cell-free homogenate and 10 μl of water was kept at 37° C. for 4 hours. The products were assayed by HVPE in the same way as in Experiment A.

As a control, the above reaction was carried out without the cell-free homogenate.

When antibiotic PS-5 was used as a substrate, no change occurred irrespective of the addition of the cell-free homogenate, which was proved by the detection of a halo at 6.5 cm to the anode (antibiotic PS-5). When the antibiotic OA-6129A was used as a substrate, on the other hand, a single antibacterial spot was located at 4.5 cm to the anode in the absence of the cell-free homogenate indicating that the substrate remained unchanged, whereas the presence of the cell-free homogenate resulted in the production of antibiotic NS-5 at 1.1 cm to the cathode.

These results demonstrate that the cell-free homogenate of *Streptomyces cremeus* subsp *auratilis* has no ability to deacetylate antibiotic PS-5, but has the ability to eliminate the pantotheinyl group from antibiotic OA-6129A.

EXAMPLE 4

Glycerol (4 g), 0.5 g of peptone, 0.2 g of glucose, 0.2 g of soluble starch, 0.5 g of Essan Miit ®, 0.5 g of dry yeast, 0.5 g of NaCl and 0.2 g of $CaCO_3$ were dissolved in 100 ml of tap water. Each 25 ml portion of the suspension was distributed in 250 ml Erlenmeyer flasks, and sterilized at 120° C. for 15 minutes. After cooling the culture medium, *Streptomyces argenteolus* was inoculated and cultivated at 28° C. for 68 hours with shaking. 20 ml of a cell extract was obtained. The same procedure of treatment as in Example 1 yielded 20 ml of a cell-free homogenate which was tested as explained in Example 3.

As in Experiment A and Examples 2 and 3, the cell-free homogenate of *Streptomyces argenteolus* has no ability to deacetylate antibiotic PS-5, but does depantothenylate antibiotic OA-6129A.

What we claim is:

1. Amidohydrolase, having the ability to depantothenylate antibiotic OA-6129A represented by the formula

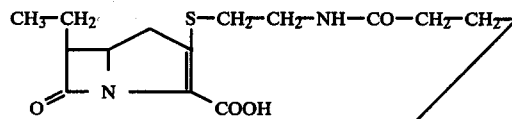
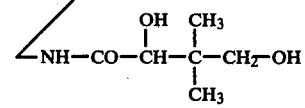

but no substantial ability to deacetylate antibiotic PS-5 represented by the formula

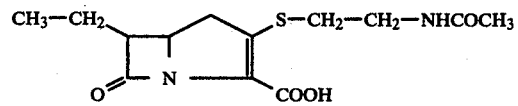

said amidohydrolase being produced by a carbapenem-producing microorganism of the genus Streptomyces.

2. The amidohydrolase of claim 1 wherein the microorganism is selected from the group of *Streptomyces fulvoviridis, Streptomyces cattleya, Streptomyces cremeus* subsp. *auratilis,* and *Streptomyces argenteolus.*

3. The amidohydrolase of claim 1 wherein the microorganism is *Streptomyces fulvoviridis* A933.

4. The amidohydrolase of claim 1 which
  (A) has the ability to depantothenylate antibiotic OA-6129A but no substantial ability to deacetylate antibiotic PS-5; the ability to deacylate N-acyl-L-amino acid; the ability to exchange the pantotheinyl group of the C-3 side chain of the OA-6129 group of antibiotics with the acyl group of acyl-CoA; and the ability to transfer the acyl group from acyl-CoA to the amino group of the C-3 cysteaminyl side chain of carbapenems and 6-aminopenicillanic acid,
  (B) has an optimum pH in the range of 7 to 7.5 and is stable at a pH in the range of 6 to 8, and
  (C) is inhibited by 0.5 to 10 mM of $Co^{++}$.

* * * * *